United States Patent [19]

Durrett et al.

[11] 4,158,362

[45] Jun. 19, 1979

[54] UNIDIRECTIONALLY VALVED DRIP CHAMBER, INLET PORT ASSEMBLY USEFUL FOR LIQUID COLLECTION CONTAINERS

[75] Inventors: Andrew M. Durrett, Libertyville; Kenneth E. Pawlak, Mundelein, both of Ill.

[73] Assignee: Abbott Laboratories, North Chicago, Ill.

[21] Appl. No.: 827,391

[22] Filed: Aug. 23, 1977

[51] Int. Cl.² .......................... A61J 1/00; A61F 5/44
[52] U.S. Cl. ..................................... 128/272; 128/275
[58] Field of Search ............... 172/272, 274, 275, 295, 172/2 F, 214 C, DIG. 24; 137/854

[56] References Cited
U.S. PATENT DOCUMENTS

| 274,308 | 3/1883 | George | 137/854 X |
|---|---|---|---|
| 3,227,173 | 1/1966 | Bernstein | 128/214 C X |
| 3,626,978 | 12/1971 | Hoekstra | 137/854 |
| 3,682,817 | 8/1972 | Marx | 137/854 X |
| 3,901,235 | 8/1975 | Patel et al. | 128/275 |

Primary Examiner—Stephen C. Pellegrino
Attorney, Agent, or Firm—Aaron L. Hardt; Robert L. Niblack

[57] ABSTRACT

A unidirectionally valved drip chamber, inlet port assembly useful for liquid collection containers, e.g., urinary collection bags, or other containers requiring antireflux protection is disclosed. The assembly comprises a flexible, hollow, substantially frusto-conical unidirectional valve fixedly mounted between the inlet and outlet of the assembly. The valve has a closed top and open bottom and is normally closed against a complementary substantially frusto-conical valve seat. The conical wall of the valve flexes away from the valve seat to allow liquid to flow from the inlet to the outlet. Liquid flowing from the outlet towards the inlet forces the valve more firmly against the valve seat so that the valve remains closed to such reverse or reflux flow.

15 Claims, 5 Drawing Figures

UNIDIRECTIONALLY VALVED DRIP CHAMBER, INLET PORT ASSEMBLY USEFUL FOR LIQUID COLLECTION CONTAINERS

BACKGROUND OF THE INVENTION

The present invention relates to unidirectionally valved drip chamber, inlet port assemblies, particularly those useful for liquid collection containers such as urinary collection bags.

The use of disposable, flexible collection containers for surgical and other applications has increased the potential for refluxion of the collected liquid back into the drainage line. In addition to inversion of the container, which can occur during transportation of the patient to and from surgery, internal or external pressures of various origins can cause the container to distort and hydrodynamically reflux the liquid. Where the flexible container is a urinary collection bag, refluxion of the collected urine can severely distend the patient's bladder thereby causing trauma and introducing bacterial infection to the bladder.

Several prior art devices have been designed to prevent the refluxion of collected liquids by the employment of a unidirectional valve. U.S. Pat. No. 3,529,599 granted to Folkman, et al. on Sept. 22, 1970 discloses a collection container for medical liquids having a disc valve. U.S. Pat. No. 3,583,401 granted to Valliancourt et al. on June 8, 1971 discloses a vented closed drainage system having a flutter valve. U.S. Pat. No. 3,626,980 granted to Svensson on Dec. 14, 1971 discloses a bacteria barrier device employing a lift valve. U.S. Pat. No. 3,901,235 granted to Patel, et al. discloses an antireflux device for urinary collection bags comprising a flap valve.

SUMMARY OF THE INVENTION

The primary object of the present invention is to provide a reliable device for the prevention of refluxion of collected liquids. More particularly, it is an object of this invention to provide a unidirectionally valved drip chamber, inlet port assembly that is useful for liquid collection containers such as flexible urinary collection bags.

In accordance with these and other objects, there is provided by the present invention a drip chamber, inlet port assembly comprising a housing having an inlet and an outlet for the entrance and exit of liquid from the housing. A substantially frusto-conical portion of the housing positioned between the inlet and outlet forms a valve seat for a flexible, hollow, substantially frusto-conical unidirectional valve fixedly mounted in the housing. The valve is open at its bottom and closed at its top. The valve is complementary to and centered within the valve seat so that the conical surface of the valve is normally in a closed position against the valve seat.

Liquid entering the inlet forces the conical surface of the valve to flex away from the valve seat, thereby opening the valve. Liquid flowing from the outlet towards the inlet forces the conical surface of the valve more firmly against the valve seat so that the valve remains closed.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
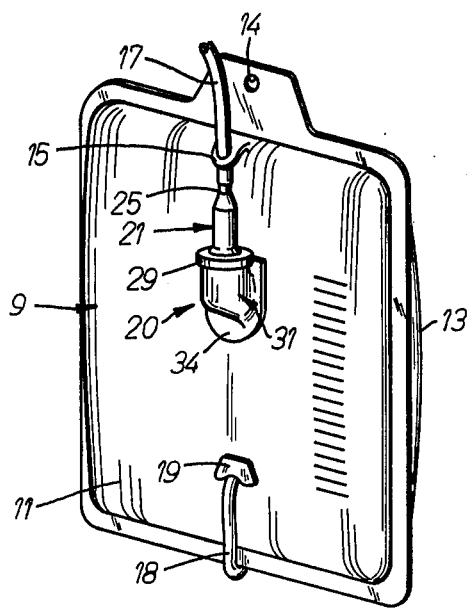
FIG. 1 is an isometric view of an embodiment of the unidirectionally valved drip chamber, inlet port assembly of this invention mounted on a flexible liquid container.

Referring to the drawing, there is shown in FIG. 1 a preferred embodiment of the unidirectionally valved drip chamber, inlet port assembly shown generally as 20 and mounted on a flexible liquid collection container shown generally as 9. A preferred use of container 9 is as a urinary collection container. Container 9 can be made of a flexible vinyl, or other suitable plastics material, and formed by the suitable sealing of a front sheet 11 to a back sheet 13, according to conventional sealing techniques well known in the art.

An upper extension of back sheet 13 includes an orifice 14 by which the container 9 may be hung. An upper extension of the front sheet 11 forms a tube holder 15 having an orifice through which a drainage tube 17 can be inserted and held. Between extensions of the bottoms of front sheet 11 and back sheet 13 an outlet tube 18 is sealed. A pocket 19 attached to the front sheet 11 removably holds the unsecured end of tube 18.

Figure 2:
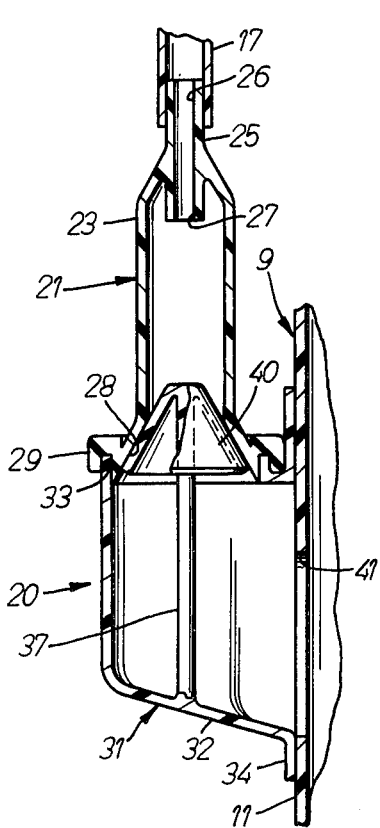
FIG. 2 is a sectional view of one embodiment of the assembly shown in FIG. 1.

A preferred embodiment of the assembly 20 is shown in section in FIG. 2. Assembly 20 can be assembled from a plurality of parts and as shown in FIG. 2 the housing thereof consists of two distinct parts, upper portion 21 and lower portion 31, which can be made of rigid vinyl plastics, polytetrafluoroethylene or other suitable materials.

Upper portion 21 includes a cylindrical drip chamber 23 and inlet tube 25. Drainage tube 17 is affixed to inlet tube 25 so that liquid flowing through drainage tube 17 enters the inlet tube 25 through inlet orifice 26. As shown in FIG. 2, inlet tube 25 preferably includes a drop former extension terminating at orifice 27. It will be apparent to those skilled in the art that either or both of the inward and outward extensions of tube 25 can be eliminated, if desired, without departing from the scope of this invention.

Upper portion 21 further includes a substantially frusto-conical portion, the inner surface of which forms a valve seat 28. As shown in FIG. 2, seat 28 is an integrally molded part of upper portion 21. However, if different release characteristics are desired for seat 28 than for the remainder of upper portion 21, seat 28 can be made separately and then affixed to upper portion 21. An annular flange 29 circumscribes the open bottom of upper portion 21.

Lower portion 31 of assembly 20 is substantially elbow-shaped and has a bottom wall 32, an orifice in its upper wall circumscribed by annular rim 33 and an orifice in its sidewall circumscribed by flange 34 which functions as the outlet by which liquid exits from assembly 20. Preferably, flange 34 and the orifice it surrounds are substantially D-shaped, as shown in FIG. 1.

As seen in FIG. 2, a shaft 37 extends upwardly from the bottom wall 32 and is molded integrally thereto. A flexible, hollow, substantially frusto-conical valve 40 is fixedly mounted on shaft 37 in a suitable manner so that valve 40 does not reciprocate thereon. For example, valve 40 can have an orifice in its upper surface through which shaft 37 extends, or valve 40 can be sealed to the top of shaft 37. Whatever manner is chosen, the upper surface of valve 40 must be impervious to liquids when the mounting is completed. Preferably, flexible valve 40 is made of a nonwettable elastomeric material, such as silicone rubber, and it may be of any thickness of sufficient strength to hold its molded, substantially frusto-conical shape when not subjected to external pressures. It will be clear to those skilled in the art that numerous shapes and configurations, such as a bell-shape, are the equivalent of a substantially frusto-conical shape.

Shaft 37 will have a predetermined position and length and valve 40 predetermined outer dimensions all chosen so that when upper portion 21 and lower portion 31 have their respective flanges 29 and 31 sealed in juxtaposition by conventional techniques well known in the art, flexible valve 40 will be complementary to and substantially centered within valve seat 28. The embodiment shown in FIG. 2 of assembly 20, preferably has lower portion 31 sealed by techniques well known in the art to the front sheet 11 of container 9, before upper portion 21 is sealed to the lower portion 31. Obviously, front sheet 11 will have an orifice 41 therethrough by which liquid can enter container 9 after it exits from assembly 20.

Figure 3:
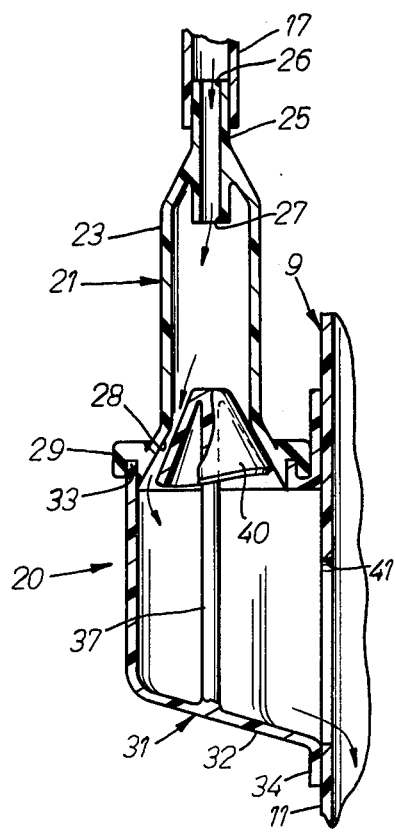
FIG. 3 is a sectional view of one embodiment of the assembly shown in FIG. 2 when the valve thereof is open.

When assembly 20 is mounted on container 9, as illustrated in FIG. 2, the conical surface of valve 40 is normally positioned against valve seat 28. As illustrated in FIG. 3, when substantial amounts of liquid enter drip chamber 23 through inlet tube 25 and contact valve 40, the conical surface of valve 40 flexes or collapses away from valve seat 28 thereby opening the valve and allowing the liquid to flow through lower portion 31 into container 9. However, liquid attempting to flow from the outlet of assembly 20 towards the inlet tube 25 forces valve 40 more firmly against seat 28 so that valve 40 remains closed and prevents reverse or reflux flow of liquid from container 9 into drainage tube 17.

Figure 4:
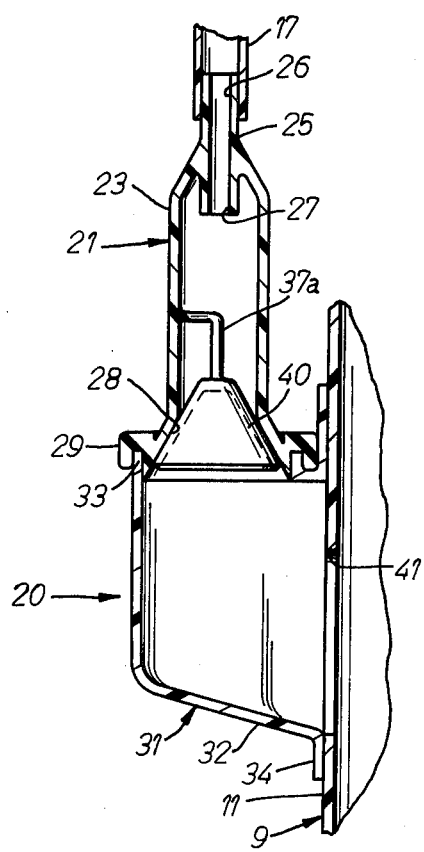
FIG. 4 is a sectional view of another embodiment of the assembly shown in FIG. 1.

FIG. 4 illustrates another embodiment of assembly 20 wherein the flexible valve 40 is fixedly mounted on a stem 37a which extends from the inner wall of drip chamber 23. This embodiment of the assembly 20 is otherwise identical to the embodiment illustrated in FIGS. 2 and 3.

Figure 5:
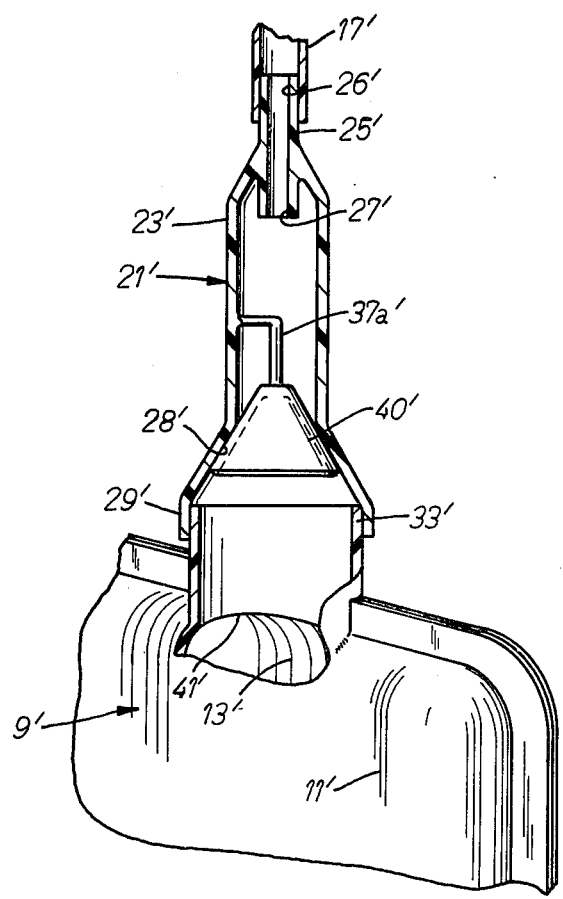
FIG. 5 is a sectional view of another embodiment of the unidirectionally valved drip chamber, inlet port assembly of this invention mounted as a neck on a flexible liquid container.

FIG. 5 illustrates still another embodiment of the unidirectionally valved drip chamber, inlet port assembly of this invention, shown generally as 20' and mounted on a liquid collection container shown generally as 9'.

Assembly 20' is sealed between front and back sheets 11', 13' of container 9' and forms a neck thereof. The housing of assembly 20' includes an upper portion 21' open at its bottom and having a drip chamber 23', drip tube 25', valve seat 28', circular bottom flange 29', shaft 37a and flexible frusto-conical valve 40' substantially identical to those described in the embodiments of assembly 20 shown in FIG. 4. However, assembly 20' as shown in FIG. 5 has a cylindrical lower portion 31' having closed sidewalls and an open top and bottom.

Preferably, lower portion 31' is sealed to container 9' by conventional techniques well known in the art, before upper portion 21' is sealed to lower portion 31' to form assembly 20'. Assembly 20' functions in the same manner as assembly 20 except for the fact that its outlet is in the bottom wall of assembly 20', while the outlet is in the sidewall of assembly 20.

Having now described the invention in specific detail and exemplified the manner in which it may be carried into practice, it will be readily apparent to those skilled in the art that innumerable variations, applications, modifications and extensions of the basic principles involved may be made without departing from its sphere or scope.

That which I claim is:

1. A drip chamber, inlet port assembly comprising:
   a housing having an inlet for the entrance of liquid into said housing, an outlet for the exit of liquid from said housing, and a substantially frusto-conical portion positioned between said inlet and outlet and forming a valve seat; and
   a flexible, hollow, substantially frusto-conical unidirectional valve fixedly mounted, on means therefor, in said housing complementary to and centered within said valve seat so that the conical surface of said valve is normally positioned against said valve seat, said valve having its top closed and its bottom open, whereby liquid flowing from said inlet towards said outlet forces said conical surface of said valve to flex away from said valve seat so that said valve is opened, while liquid flowing from said outlet towards said inlet forces said conical surface of said valve more firmly against said valve seat so that said valve remains closed to such reverse flow.

2. The drip chamber, inlet port assembly as defined in claim 1 wherein said inlet is formed by a tube for connecting said assembly to a liquid source.

3. The drip chamber, inlet port assembly as defined in claim 2 wherein said tube forming said inlet extends inwardly and outwardly of said housing.

4. The drip chamber, inlet port assembly as defined in claim 1 wherein said valve is fixedly mounted within said housing on a shaft integrally affixed to said housing at a position below said valve.

5. The drip chamber, inlet port assembly defined in claim 1 wherein said valve is fixedly mounted within said housing on a shaft integrally affixed to said housing at a position above said valve.

6. The drip chamber, inlet port assembly defined in claim 1 wherein said outlet is surrounded by a flange on said housing for the attachment of said assembly to a container.

7. The drip chamber, inlet port assembly defined in claim 6 wherein said outlet is located in a sidewall of said housing.

8. The drip chamber, inlet port assembly defined in claim 7 wherein said outlet and flange are respectively substantially D-shaped.

9. The drip chamber, inlet port assembly defined in claim 1 when affixed to a liquid container having an orifice thereinto in communication with said outlet of said assembly.

10. The combination defined in claim 9 wherein said container is a closed flexible plastic bag.

11. The combination defined in claim 10 wherein said assembly is affixed to the front wall of said container.

12. The combination defined in claim 10 wherein said drip chamber and inlet port assembly forms a neck on said container and has said outlet located in the bottom wall of said housing.

13. A drip chamber, inlet port assembly comprising: a housing having a tubular inlet for the entrance of liquid into said housing, a substantially D-shaped outlet for the exit of liquid from said housing, said outlet located in a sidewall of said housing and surrounded by a substantially D-shaped flange on said housing for the attachment of said assembly to a container, and a substantially frusto-conical portion positioned between said inlet and outlet and forming a valve seat; and a flexible, hollow, substantially frusto-conical unidirectional valve fixedly mounted, on means therefor, in said housing complementary to and centered within said valve seat so that the conical surface of said valve is normally positioned against said valve seat, said valve having its top closed and its bottom open; whereby liquid flowing from said inlet towards said outlet forces said conical surface of said valve to flex away from said valve seat so that said valve is opened, while liquid flowing from said outlet towards said inlet forces said conical surface of said valve more firmly against said valve seat so that said valve remains closed to such reverse flow.

14. The drip chamber, inlet port assembly defined in claim 13 when affixed to a liquid container having an orifice thereinto in communication with said outlet of said assembly.

15. The combination defined in claim 14 wherein said container is a closed flexible plastic bag and said drip chamber and inlet port assembly is affixed to the front wall of said container.

* * * * *